(12) United States Patent
Kleppe et al.

(10) Patent No.: US 10,515,631 B2
(45) Date of Patent: Dec. 24, 2019

(54) SYSTEM AND METHOD FOR ASSESSING THE COGNITIVE STYLE OF A PERSON

(71) Applicant: KONINKLIJKE PHILIPS N.V., Eindhoven (NL)

(72) Inventors: Mieke Kleppe, Eindhoven (NL); Tim Johannes Willem Tijs, Stramproy (NL); Lysanne Sloff, Nijmegen (NL); Georgio Mosis, Shanghai (CN); Joyca Petra Wilma Lacroix, Eindhoven (NL); Joris Hendrik Janssen, Eindhoven (NL); Jan Tatousek, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/102,535

(22) PCT Filed: Dec. 11, 2014

(86) PCT No.: PCT/EP2014/077459
§ 371 (c)(1),
(2) Date: Jun. 8, 2016

(87) PCT Pub. No.: WO2015/091223
PCT Pub. Date: Jun. 25, 2015

(65) Prior Publication Data
US 2016/0314784 A1    Oct. 27, 2016

(30) Foreign Application Priority Data

Dec. 17, 2013  (EP) .................................. 13197733
Jun. 27, 2014  (EP) .................................. 14174775

(51) Int. Cl.
*A61B 5/16* (2006.01)
*G10L 25/51* (2013.01)
(Continued)

(52) U.S. Cl.
CPC .............. *G10L 15/19* (2013.01); *A61B 5/167* (2013.01); *A61B 5/4803* (2013.01); *G10L 17/26* (2013.01);
(Continued)

(58) Field of Classification Search
CPC .... G06F 17/27; G06F 17/2705; G06F 17/271; G06F 17/2715; G06F 17/272;
(Continued)

(56) References Cited

U.S. PATENT DOCUMENTS 4,974,191 A * 11/1990 Amirghodsi .......... G06F 17/277
380/1
5,302,132 A * 4/1994 Corder .................... G09B 5/14
345/173
(Continued)

FOREIGN PATENT DOCUMENTS

WO      9963462 A1   12/1999

OTHER PUBLICATIONS

Kellner et al, "Extracting Knowledge About Cognitive Style", 7th International Conference on Engineering, 2011, pp. 73-79
(Continued)

*Primary Examiner* — Dwayne D Bost
*Assistant Examiner* — Stephen M Brinich

(57) ABSTRACT

The present invention relates to a system and method for assessing the cognitive style of a person. The system comprises an input interface (12) for receiving speech spoken by the person, a language processor (16) for analyzing the speech to identify predetermined natural language elements, and a style identifier (18, 18') for identifying the cognitive style of the person based on the identified natural language elements.

17 Claims, 10 Drawing Sheets

(51) Int. Cl.
*G10L 25/63* (2013.01)
*G10L 15/18* (2013.01)
*G10L 15/19* (2013.01)
*A61B 5/00* (2006.01)
*G10L 17/26* (2013.01)
*G10L 25/90* (2013.01)

(52) U.S. Cl.
CPC .............. *G10L 25/51* (2013.01); *G10L 25/63* (2013.01); *G10L 15/18* (2013.01); *G10L 2025/906* (2013.01)

(58) Field of Classification Search
CPC .............. G06F 17/2725; G06F 17/273; G06F 17/2735; G06F 17/274; G06F 17/2745; G06F 17/275; G06F 17/2755; G06F 17/276; G06F 17/2765; G06F 17/277; G06F 17/2775; G06F 17/278; G06F 17/2785; G06F 17/279; G06F 17/2795; G06F 17/2827; G06F 17/2818; G06F 17/2854; G06F 17/2881
USPC ........ 704/1–10, 257–260, E15.003, E15.004
See application file for complete search history.

(56) References Cited

U.S. PATENT DOCUMENTS

| | | | | |
|---|---|---|---|---|
| 5,572,421 A * | 11/1996 | Altman | ............... | G06F 19/3431 705/2 |
| 5,642,731 A * | 7/1997 | Kehr | ............... | A61J 7/0481 600/300 |
| 5,908,383 A * | 6/1999 | Brynjestad | ............... | G06F 19/345 128/920 |
| 7,548,846 B1 * | 6/2009 | Monster | ............... | G06F 9/4448 704/8 |
| 2003/0163299 A1 * | 8/2003 | Iliff | ............... | G06F 19/324 704/1 |
| 2003/0172052 A1 | 9/2003 | Crandell et al. | | |
| 2004/0215453 A1 * | 10/2004 | Orbach | ............... | G10L 15/005 704/231 |
| 2007/0271086 A1 * | 11/2007 | Peters | ............... | G06F 17/211 704/9 |
| 2008/0059145 A1 * | 3/2008 | Wood | ............... | G09B 19/06 704/2 |
| 2009/0140864 A1 | 6/2009 | Aaron et al. | | |
| 2010/0075289 A1 | 3/2010 | Maher et al. | | |
| 2011/0054985 A1 | 3/2011 | Ricci et al. | | |
| 2012/0179449 A1 * | 7/2012 | Raskino | ............... | G06F 17/30719 704/2 |
| 2012/0246054 A1 | 9/2012 | Sastri | | |
| 2013/0346077 A1 * | 12/2013 | Mengibar | ............... | G10L 15/265 704/235 |
| 2014/0316765 A1 * | 10/2014 | Fitterer | ............... | G06F 17/2775 704/9 |
| 2016/0293159 A1 * | 10/2016 | Belisario | ............... | G10L 15/07 |

OTHER PUBLICATIONS

Valllacher et al, "Levels of Personal Agency: Individual Variation in Action Identification", Journal of Personality and Social Psychology, vol. 57, No. 4, 1989, pp. 660-671.
Chen, "Web-Based Learning Programs: Use by Learners With Various Cognitive Styles", Computers & Education, vol. 54, 2010, pp. 1028-1035.
Bental et al, "Patient Information Systems That Tailor to the Individual", Patient Education and Counseling, vol. 36, Issue 2, 1999, pp. 171-180.
Hubert, "Cognitive Style As a Basis for MIS and DSS Designs: Much ADO About Nothing?", Management Science, vol. 29, No. 5, 1983, pp. 567-576.
Ryan et al, "Development and Performance Usability Testing of a Theory-Based, Computerized, Tailored Intervention", Computers, Informatics, Nursing, Vol. 27, No. 5, 2009, pp. 288-298.
Baker, "The Meaning and the Measure of Health Literacy", Journal of General Internal Medicine, vol. 21, 2006, pp. 878-883.

* cited by examiner

SYSTEM AND METHOD FOR ASSESSING THE COGNITIVE STYLE OF A PERSON

CROSS-REFERENCE TO PRIOR APPLICATIONS

This application is the U.S. National Phase application under 35 U.S.C. § 371 of International Application No. PCT/EP2014/077459, filed on Dec. 11, 2014, which claims the benefit of European Patent Application No. 13197733.2, filed on Dec. 17, 2013 and European patent Application No. 14174775.8, filed on Jun. 27, 2014. These applications are hereby incorporated by reference herein.

FIELD OF THE INVENTION

The present invention relates to a system and a corresponding method for assessing the cognitive style of a person. The present invention relates further to a computer program for implementing said method.

BACKGROUND OF THE INVENTION

Medication non-adherence is a multifaceted issue, which brings major health risks and healthcare costs with it. Decennia of research have led to the identification of a wide range of determinants for non-adherence. Existing technology-based solutions (e.g., alarm systems) as well as more traditional solutions (e.g., weekly pill box, information leaflets) to promote adherence often address a subset of these determinants using a one-size-fits-all approach. As such, these solutions fail to acknowledge the individual differences between patients. Face to face meetings between the patient and the medical professional allow for a more personalized approach in which the medical professional can assess the needs, interests and situation of the patient and apply a tailored intervention (e.g., health promotion information) that addresses the knowledge and motivation deficits of the patient.

While these types of interventions tailored to the individual have shown to be considerably more effective than generic solutions, they still establish only a moderate effect on adherence. One reason for this could be that the tailoring is limited to the intervention content (e.g., the type of information that is provided), but the communication and information in the intervention is still delivered in a one-size-fits-all format. An enormous amount of research underscores the major differences between individuals in cognitive style (also referred to as "profile" hereinafter), i.e., the way that individuals think, perceive and process information. Matching the information delivery style of an adherence intervention to a person's cognitive style is expected to improve the effect of these solutions. This matching would require that (1) the patient's cognitive style will be assessed and (2) the information/communication delivery style is adapted accordingly.

The assessment of cognitive style poses a major challenge to the medical care professional, due to the fact that a person's cognitive style is not easily identifiable. Moreover, when known, it requires a specific type of knowledge about cognitive style to be able to adapt the intervention effectively.

Traditionally, cognitive style is assessed with the use of questionnaires (e.g., the Myers-Briggs Type Indicator (MBTI) is generally known and widely used instrument for assessing cognitive style). However, using questionnaires in the clinical context would be obtrusive to the patient and disruptive for the clinical workflow. It is known that certain dimensions of cognitive style can also be assessed using the analysis of natural language. This method is very time-consuming when it needs to be done manually by experts.

As for the assessment of cognitive style, the recommendations to tailor interventions/communication to the cognitive style are often unknown to the medical care provider and are quite time consuming to discover. Further, the known methods for eliciting cognitive style impose a burden to the patient, entailing the filling out of extensive questionnaires. Also, assessment by the care provider requires a specific expertise and a considerable amount of time. Moreover, care providers often lack the specific expertise to effectively adapt their style to different types of cognitive styles. Altogether, this leads to a missed opportunity to tailor an intervention to the cognitive style of the specific patient under consideration.

US 2010/075289 A1 discloses a method and system for automated customization of original content for one or more users. One implementation involves obtaining behavior information for a user, profiling the user based on the user behavior information, determining a preferred learning style for the user based on the user profiling, and customizing the original content based on the preferred learning style for the user. Profiling the user may involve analyzing the user behavior information using one or more profiling patterns for profiling the user to determine scores for different behavior categories for the user. Customizing the original content may involve determining a preferred learning style for the user based on the user profiling, and further includes selecting a customization scheme from a scheme repository, based on said scores for different behavior categories for the user, and applying the selected customization scheme to the original content to generate customized content for the user.

SUMMARY OF THE INVENTION

It is an object of the present invention to provide a system and a corresponding method for assessing the cognitive style of a person, which overcome the above mentioned shortcomings and particular allow an easy, efficient and, preferably, unobtrusive way for assessing the cognitive style of a person.

In a first aspect of the present invention a system for assessing the cognitive style of a person is presented comprising:

an input interface for receiving speech spoken by the person, a language processor for analyzing the speech to identify predetermined natural language elements, a style identifier for identifying the cognitive style of the person based on the identified natural language elements, a recommendations generator for generating recommendations how to tailor the communication and/or information delivery style to be provided to the person according to the identified cognitive style of the person and an output interface for outputting the identified cognitive style and/or the generated recommendations.

In a further aspect of the present invention a method for assessing the cognitive style of a person is presented comprising:

receiving speech spoken by the person, analyzing the speech to identify predetermined natural language elements, identifying the cognitive style of the person based on the identified natural language elements, generating recommendations how to tailor the communication and/or information delivery style to be provided to the person according to the identified cognitive style of the person and outputting the identified cognitive style and/or the generated recommendations.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed system and as defined in the dependent claims.

The present invention is based on the idea of derivation of cognitive style from natural language, based on which recommendations for tailoring the delivery style to the identified cognitive style can be reliably made. A number of natural language elements have been identified based on which the cognitive style can be derived. The invention operates by analyzing the speech to identify the natural language elements that are indicative of the cognitive style, which is then indicated to the user (e.g., care provider), for instance in form of a style indicator. In addition, in a preferred embodiment, the recommendations that correspond to the identified cognitive style are delivered to the user.

The proposed system and method provide a quick and easy way for care providers to indicate their patients' cognitive style at the point of service, and a set of recommendations to tailor their communication/information delivery style to the cognitive style of the patient. Accordingly, the system further comprises a recommendations generator for generating recommendations how to tailor communication and/or information, in particular healthcare and guidance information, to be provided to the person according to the identified cognitive style of the person. As a consequence the effectiveness of therapeutic intervention strategies can be improved.

In an exemplary embodiment the communication style in a face-to-face conversation is adapted. This may entail for example that the user, e.g. a healthcare professional, is guided to adopt an empathic style for a person that has a sensitive personality. Further, recommendations may be made which tone of voice and which type of language would be appropriate for this person (e.g. use soft tone of voice, show empathy by summarizing the feelings expressed by the patient, acknowledge how difficult it is, etc.).

Preferably, the speech (i.e. the spoken language) is first translated into text so that in the subsequent step the spoken language and/or the text is analyzed to identify the natural language elements.

For outputting the identified cognitive style and/or the generated recommendations for use by a device or a user, in particular a caregiver (also called healthcare provider or healthcare professional), for tailoring communication and/or information, in particular healthcare and guidance information, to be provided to the person an output interface is provided. Said output interface may, e.g., be a display, for instance on a patient monitor, the care provider's computer screen, smartphone or tablet. Other output interfaces, such as loudspeakers, may also be used.

Advantageously, said language processor is configured to determine in the received speech and/or the text one or more of the amount and/or length of pauses,
the length of sentences and/or words,
the amount of words in a sentence,
the amount of personal pronouns and/or possessive pronouns,
the amount of verbs, nouns and/or adjectives,
the amount of words with predetermined prefixes and/or endings,
the amount of layman's words or phrases,
the amount how much the person speaks about a predetermined topic,
the extent to which the person uses predetermined words or phrases,
the percentage of second person words,
the variance in pitch.

It has been found that such natural language elements in speech and/or text are correlated to the cognitive style of a person so that their evaluation is useful in determining the cognitive style of a person. Other natural language elements, that may e.g. only become apparent through future research, may be used as well.

Preferably, said translator is configured to determine the language of the received speech, wherein said language processor is configured to analyze the text to identify predetermined natural language elements of the determined language. The language of the speech is, e.g., important in order to select appropriate natural language elements which, in this language, are useful in determining the cognitive style of a person.

In another embodiment the system further comprises a style database comprising a plurality of cognitive styles and corresponding natural language elements, wherein said style identifier is configured to access said style database and select the cognitive style of the person based on the identified natural language elements. The style database is preferably predetermined, but can also be updated over time as a kind of learning system. The use of a style database provides a simple and quick method for determining the cognitive style.

In a further embodiment said style identifier comprises a rule based engine for determining dimensions of the cognitive style of the person based on the identified natural language elements. For example, as dimensions of the cognitive style Fighter, Analyst, Optimist, and Sensitive may be used. Alternatively, known cognitive style dimensions may be taken as a starting point, e.g. the 'need for cognition', 'consideration of future consequences', 'Locus of Control', as will be explained below in more detail. A rule based engine is generally known in the art. A description and of its working principle can currently be found under link http://en.wikipedia.org/wiki/Rule-based_system.

Preferably, the system further comprises a recommendations database comprising a plurality of recommendations and corresponding cognitive styles, wherein said output interface is configured to access said recommendations database and select the recommendations based on the identified cognitive style of the person. The recommendations database is preferably predetermined, but can also be updated over time as a kind of learning system. The use of a recommendations database provides a simple and quick method for determining the recommendations. Thus, the main idea is that these recommendations are stored in a database. The system finds the right set of recommendations based on the processed natural language and presents these to the healthcare provider in an actionable format, e.g. on his computer screen.

The input interface preferably comprises a data interface for receiving audio data files of recorded speech and/or an audio recording unit, in particular a microphone, for converting spoken speech into electric speech signals. Thus, the speech may be recorded on the fly, or the speech may be prerecorded and evaluated at a later time.

In another embodiment said input interface further comprises an interrogator for interrogating the person. Thus, the system provides questions, e.g. on a display or as spoken questions, to the person, which the person has to answer (by vocalizing the answer) so that the system can process the speech as explained above. The interrogator is preferably implemented on a computer, e.g. as a corresponding software, and may be adapted to the person. Further, the interrogator may evaluate the given answers and adapt the next questions accordingly in order to get as much useful speech as possible in order to determine the person's cognitive style as reliably as possible. Alternatively, the questions of the interrogator are presented as a recommendation for the user (e.g. the healthcare provider) to be asked by the user himself (rather than letting them be asked by the interrogator). This would allow for a more natural conversation.

The present invention is not limited to the evaluation of speech and text derived from speech. In addition, other information obtained from the person or about the person, such as video data or physiological information, can be used to further improve the determination of the person's cognitive style. Accordingly, in an embodiment said input interface further comprises a video data interface for receiving image data files containing image data of the person and/or an imaging unit, in particular a camera, for recording image data of the person, wherein the system further comprises a video processor for analyzing the image data to identify predetermined image elements, and wherein said style identifier is configured to identify the cognitive style of the person based on the identified natural language elements and the identified image elements. Such image data may e.g. be video features of facial expressions, posture, gestures of the person which are evaluated in addition to the natural language elements.

In another embodiment said input interface further comprises a physiological data interface for receiving physiological data files containing physiological data of the person and/or an physiological data unit, in particular physiological data sensors, for recording physiological data of the person, wherein the system further comprises a physiological data processor for analyzing the physiological data to identify predetermined physiological data elements, and wherein said style identifier is configured to identify the cognitive style of the person based on the identified natural language elements and the identified physiological data elements. For instance, when a certain topic is discussed, physiological data (i.e. a vital sign such as heart rate, breathing rate, etc.) may be indicative of the emotional response to that topic and thereby be indicative of the person's cognitive style.

It is generally not possible to exactly indicate the correct cognitive style of the person. This may even be changing over time, e.g. during an interrogation. Hence, in an embodiment, additional information, like the most dominant momentary cognitive style of the person and a momentary certainty level indicating the likelihood of the identified cognitive style being the most dominant style, is identified by the style indicator.

Accordingly, in an embodiment said output interface is configured to output an indication of the most dominant cognitive style of the person and the certainty level and to update this indication over time according to changes of the cognitive style and/or the certainty level. For instance, a displayed indication of the most dominant cognitive style of the person and the certainty level may change, e.g. in color, size, etc. when the most dominant cognitive style of the person and/or the certainty level changes.

The system may further comprise an optimizer for determining the information entropy of one or more possible next questions which may be used for interrogating the person and for selecting the possible next question providing the highest information entropy. Thus, the next question(s) to be used is (are) actively selected in order to obtain as much information as possible that is useful in determining the person's cognitive style. This selection of the next question(s) generally depends on the previously asked questions and thus represents a continuously adaptive and learning system.

It should be noted that the present invention is not only directed to assessing the cognitive style of a patient for use by a care provider, but can be generally used for assessing the cognitive style of any person. Hence, whenever reference is made herein to a "patient" this shall be generally understood as a "person". Similarly, a user shall be understood broadly, and whenever reference is made herein to a "care provide" this shall be generally understood as a "user". In principle, the present invention may be used in any situation where two persons communicate and it is essential that information provided by one of the two persons (e.g., by a healthcare professional, teacher, parent, sales person, etc., i.e. generally a "user" or information provider) is received well by the other person (e.g., by a patient, student, child, buyer etc., i.e. generally a "person" or information receiver).

In another preferred embodiment said style identifier comprises one or more expert systems, each for performing a two-class classification for classifying if the person falls into one particular cognitive style or not. Each expert system may use one or more machine learning models that have been found most useful for the classification if a person fits into a particular cognitive style or not. The cognitive styles (profiles) are e.g. Analyst, Fighter, Sensitive and Optimist. Other cognitive styles may be e.g. Knowledge, Activity, Struggle and Enjoyment. As a further improvement said style identifier comprises two or more expert systems and a gating model unit for determining the final classification from the two-class classifications performed by the two or more expert systems. The classification result and its reliability can thus be further improved.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
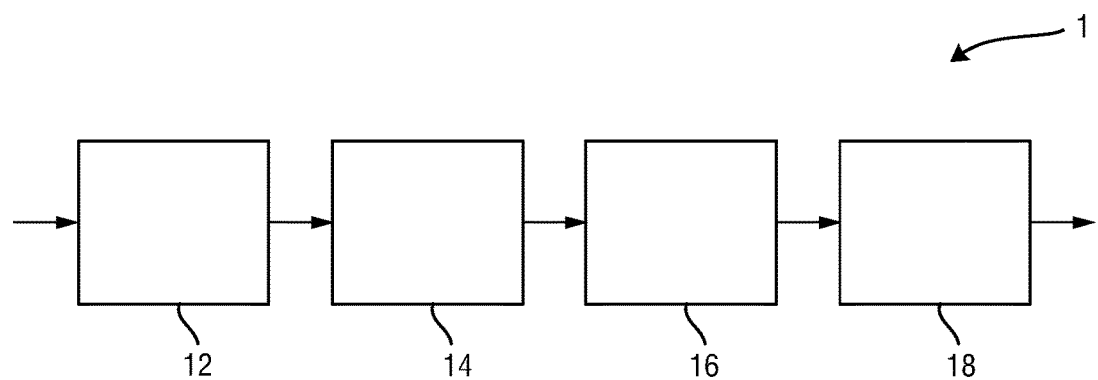
FIG. 1 shows a schematic diagram of a first embodiment of a system according to the present invention.

FIG. 1 shows a schematic diagram of a first embodiment of a system 1 for assessing the cognitive style of a person according to the present invention. It comprises an input interface 12 for receiving speech spoken by the person. The input interface is, in this embodiment, a data port for receiving audio files (e.g. an MP3 file, a MIDI file, etc.) or audio data in any other format, which audio data represents the speech spoken by the person. Said audio data may be prerecorded or may just be received from a microphone, which records the speech currently spoken by the person.

The system 1 further comprises an optional translator 14 for translating the received speech into text. This may be implemented by a known algorithm, as e.g. used in dictation systems or speech recognition systems used in automated call centers. Many of such speech recognition algorithms are known and used in practice, which may generally be used by the translator 14.

The system 1 further comprises a language processor 16 for analyzing the speech and/or text to identify predetermined natural language elements. Such predetermined natural language elements include one or more of the amount and/or length of pauses, the length of sentences and/or words, the amount of words in a sentence, the amount of verbs, nouns, adjectives and/or possessive pronouns, the amount of words with predetermined prefixes and/or endings (e.g., if the language is English, the number words ending with "ed" versus the number of words ending with "ing"), the amount of layman's words or phrases, the amount how much the person speaks about a predetermined topic, the extent to which the person uses predetermined words or phrases.

Still further, the system 1 comprises a style identifier 18 for identifying the cognitive style of the person based on the identified natural language elements. This style identifier 18 may be implemented by use of a look-up table listing natural language elements and the corresponding cognitive style. In another embodiment said style identifier 18 is implemented as a rule-based style identification engine.

The various units of the system 1 may be comprised in one or multiple digital or analog processors depending on how and where the invention is applied. The different units may completely or partly be implemented in software and carried out on a personal computer which is connected to source of speech spoken by the person, e.g. to a microphone or to a storage storing an audio file included prerecorded speech. Some or all of the required functionality may also be implemented in hardware, e.g. in an application specific integrated circuit (ASIC) or in a field programmable gate array (FPGA).

Figure 2:
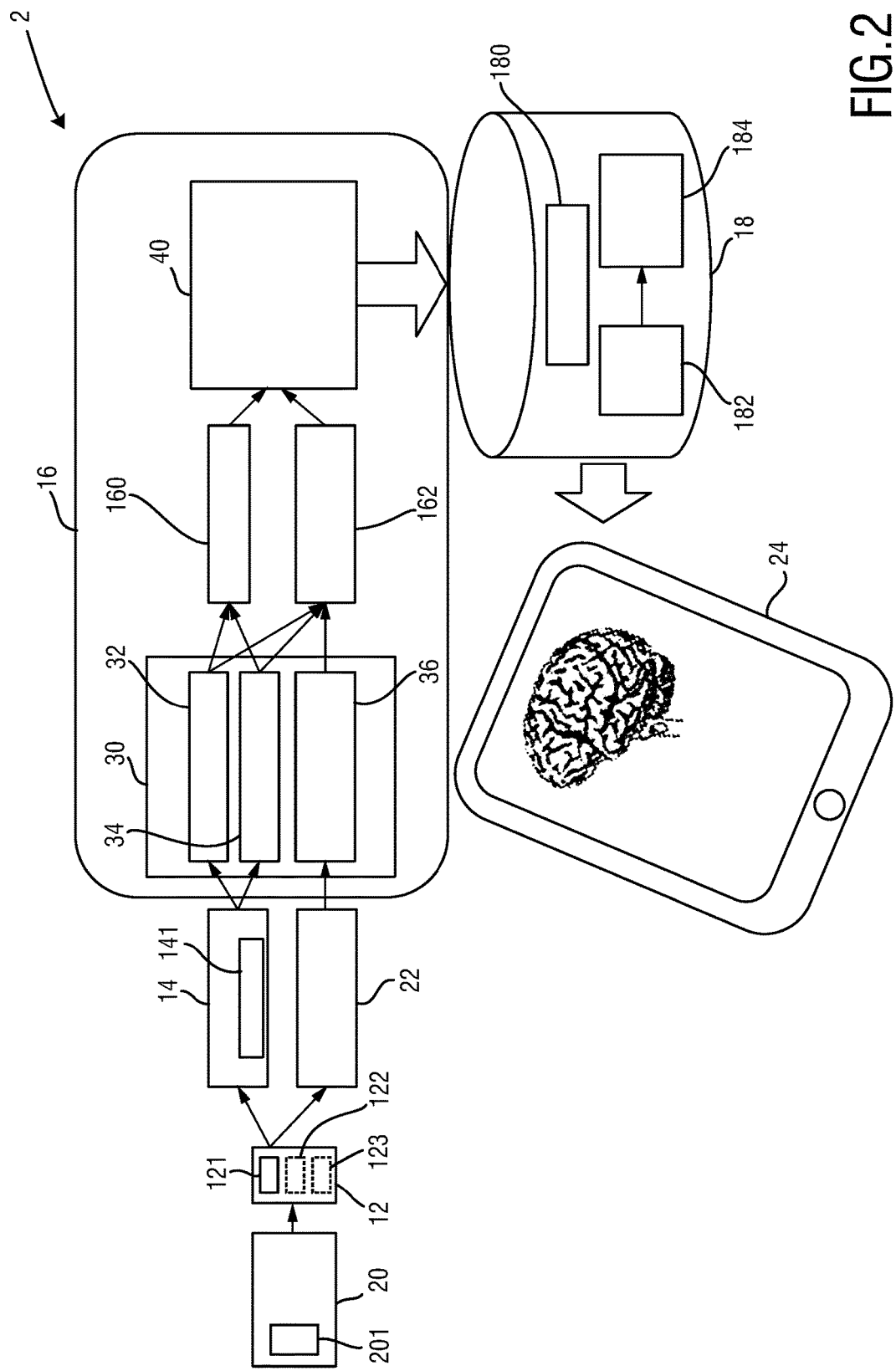
FIG. 2 shows a schematic diagram of a second embodiment of a system according to the present invention.

A schematic diagram of a more detailed embodiment of a system 2 is shown in FIG. 2. In this embodiment the system 2 comprises an apparatus 20 (e.g. a mobile phone) with a microphone 201 for recording and, preferably, storing audio files of recorded speech of the person, e.g. a patient in a hospital or at a care provider. The audio files are provided, e.g. via a data cable or wirelessly (e.g. using a wireless transmission technique like Bluetooth, WLAN or Zigbee), to the input interface 12 comprising an audio data interface 121 for receiving audio data from the apparatus 20. The input interface 12 is connected to the translator 14 for converting the speech recorded in the audio files into written understandable text. In parallel a speech pattern analyzer 22 is provided for analyzing the speech patterns contained in the speech. Preferably, the translator 14 is configured to or comprises a unit 141 for determining the language (e.g. Dutch, English, etc.) of the received speech.

It shall be noted here that additional data, such as video data (e.g. from a camera) and physiological data (e.g. from vital sign sensors) of the person may be used in addition to speech for determining the person's cognitive style. In this case the input interface 12 comprises an additional video data interface 122 and a physiological data interface 123 as indicated in FIG. 2 by broken lines.

The results of the translator 14 and the speech pattern analyzer 22 are provided to the language processor 16 as speech analysis result 30 including the text 32 received from the translator 14, the language 34 of the speech and the speech pattern and pause information 36. Based on this speech analysis result 30 the language processor 16 determines word statistics in a text evaluation unit 160 and performs content processing in a content processing unit 162. From these processing steps 40 are obtained.

A rule-based style identifier (SI) 18 identifies the cognitive style based on the output (i.e. the natural language elements 40) of the language processor 16. In particular, the person-specific input obtained from the language processor 16 and a rule-based engine 180 are used in the style identifier 18, to determine, based on psychographic rules that operate on the input from the language processor, specific dimensions of cognitive style of the patient captured in the audio file turned into text. Further, person-specific input (e.g. video data or physiological data) obtained via a user interface 24 (e.g. a computer, tablet, smartphone, etc.) may be used for this identification.

The user interface (UI) 24 provides the results of the analysis, i.e. the style indicator indicating the cognitive style of the person, for instance to the care provider. Preferably, recommendations to tailor communication and information to be provided to the person in an intervention are provided along with the style indicator. These recommendations may be stored in a recommendations database 182, e.g. within the style identifier 18 or external to the style identifier, said database storing recommendations for the various possible cognitive styles. Further, a recommendations generator 184 for generating (or selecting) recommendations based on the determined cognitive style may be provided.

The results and recommendations can be fine-tuned when the recorded natural speech collection of the specific persons builds up over time and the accuracy of the results increases. An extendable user interface may show the outcome of the analysis. For instance, characteristics could be added and removed. Further, the system may be configured to only determine if a person is either "extrovert" or "introvert", or the system may be extended to determine more characteristics. Additionally, the system could provide tailored information or provide guidelines for the healthcare providers on which interventions could be most effective for the particular person.

Figure 3:
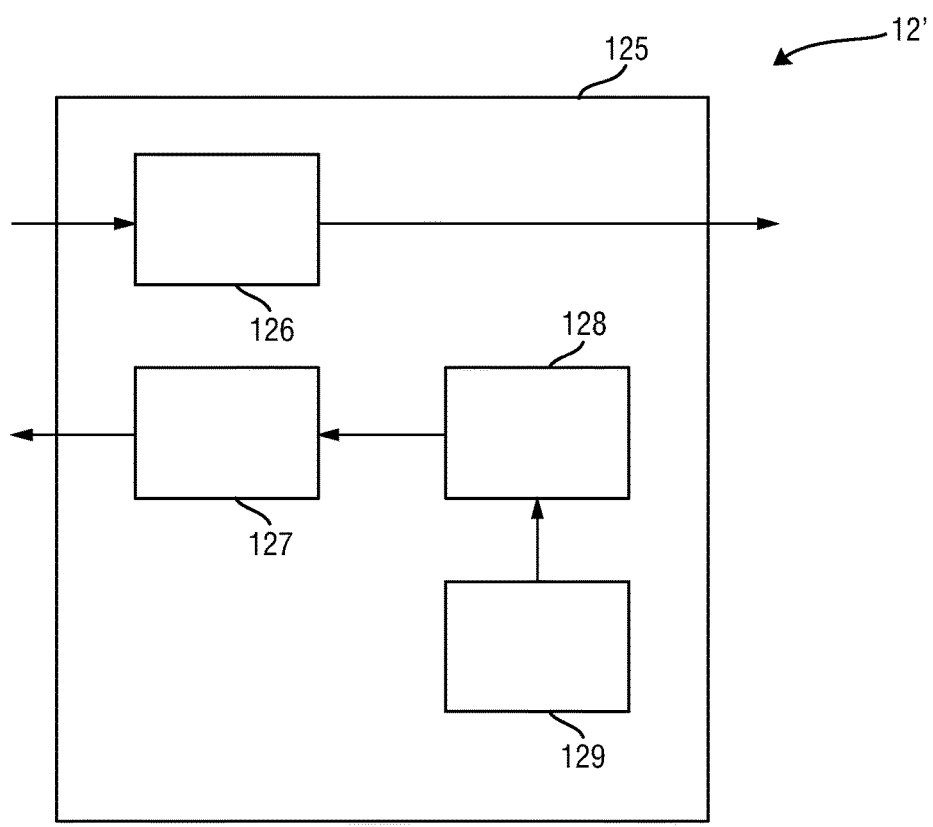
FIG. 3 shows a schematic diagram of an embodiment of an input interface.

A schematic diagram of another embodiment of the input interface 12' depicted in FIG. 3. In this embodiment the input interface does not only record audio data but also is also able to output audio data. For this purpose the input interface 12' comprises an interrogator 125. Said interrogator 125 comprises a microphone 126 for recording speech and a speaker 127 for outputting speech and asking questions to the person. The questions may be stored in a storage 128 and are e.g. selected by a control unit 129. This is a potentially effective approach because the control unit 129 can select the specific questions that are most relevant toward fast and accurate classification of the patient's cognitive style.

Preferably, open ended questions are asked by the interrogator 125 to the person so that the person needs to answer the questions by using natural speech including not only a single word like "yes" or "no".

In other embodiments of the input interface not including an interrogator the person is not asked certain questions by the system, but the system simply records any speech by the person, e.g. from a talk with a visitor, a care provider or any other person, and evaluates said speech.

In a very simple example the length of pauses in the speech of a person is evaluated. If e.g. the length of pauses is larger than a predetermined time, e.g. longer than 2 seconds, then it is judged that the person is introverted; otherwise the person is judged to be extraverted. In the first case the output of the style identifier for use by the care provider may be the following information: "This person is introverted and thinks in an abstract way. Explain why this medication is important to the patient. Provide a leaflet with written communication."

In preferred embodiments the system, in particular the language processor 16, is configured to take potential cognitive styles into account and is adapted to be able to determine natural language elements that are typical for such cognitive styles and help in the identification of such cognitive styles.

For instance, the need for cognition (NfC) can be identified in an embodiment. People high in NfC are more inclined to process relevant arguments whereas people low in NfC are more focused on peripheral cues. People low in NfC are also more likely to rely in stereotypes alone in judging other people. Hence, in an embodiment the language processor 16 is adapted to identify words/expressions related to the content of the disease in order to determine to what extent a person speaks about the disease (symptoms, consequences, underlying working, etc.) or other matters (e.g., hobbies, other people) in a given period. Further, the language processor 16 may be adapted to identify the extent to which a person uses terminology. These words/phrases can be pre-set in a database, e.g., "cardiovascular" is considered as higher on terminology than "heart", and "medication" is considered higher on terminology than "pills". Still further, the language processor 16 may be adapted to identify the extent to which a person uses typical layman's words/phrases, such as "things" and "I don't know".

As another instance, the Locus of Control (LoC) can be identified in an embodiment. LoC is about the extent to which people believe that they can control events that affect them. People with high internal LoC believe that events in2 their life derive primarily from their own actions. For example, if a person with a high internal LoC does not perform as well as they wanted to on a test, they would blame it on lack of preparedness on their part. Oppositely, if a person with a high external LoC does poorly on a test, he might attribute this to the difficulty of the test questions. Hence, in an embodiment the language processor 16 is adapted to identify the extent to which a person uses personal and possessive first person pronouns (e.g., 'my doctor' vs. 'the doctor', or 'I' versus 'they'). Patients that use many personal and possessive pronouns are generally higher on internal LoC.

For instance, for an example for the cognitive style construct of Locus of Control the rule-based engine may include a rule that decides based on the frequency of use of personal and possessive first-person pronouns whether someone has an internal or external Locus of Control. For example:

IF (number of personal first-person pronouns+first-person possessive pronouns)/(total number of words expressed) >c (constant)
THEN Locus of Control=internal
ELSE Locus of Control=external.

As still another instance, the consideration of future consequences (CFC) can be identified in an embodiment. CFC is about the extent to which individuals consider the potential future outcomes of their current behavior and the extent to which they are influenced by the imagined outcomes. Hence, in an embodiment the language processor 16 is adapted to identify the extent to which a person uses high-CFC words such as "consequences", "future", "outcome", "expect", "predict" and "anticipate".

In the above several embodiments of the system according to the present invention for determination of a patient's cognitive style based on natural language processing have been described. These embodiments are generally based on speech of the person, for instance in a conversation between the person (e.g. a patient) and the healthcare provider (or professional; HCP) or in an interrogation between the system and the person. This speech of the person is preferably triggered by open-ended questions provided by the system. Although helpful, this system is still fairly obtrusive, requiring dedicated (costly) time of the patient and the healthcare provider. In the following further embodiments are described, which are improved in this respect.

As explained above a tailored information approach is advantageous, because knowledge about a patient's cognitive style can help the healthcare provider to tailor information and/or information-style to the patient and to optimize patient experience and patient adherence. Further, many healthcare provider-patient conversations have a standard format, in which the healthcare provider has limited time to ask a predetermined number of questions to or to discuss a predetermined number of matters with the patient.

Further embodiments of a system according to the present invention are thus directed to minimize the patient-healthcare provider burden in identification of the patient's cognitive style by combines obtrusive identification methods with unobtrusive methods to use the costly (but effective) obtrusive methods when deemed necessary by the healthcare provider and/or employing uncertainty and/or information entropy data, to identify the patient's cognitive style as fast or with as little use of resources as possible, as will be explained below.

These further embodiments aim at minimizing the uncertainty about the cognitive style of a patient based on processing the spoken language extracted from healthcare provider—patient communication and guiding the healthcare provider in triggering a specific dialogue that will lead to information most likely to decrease the uncertainty. For this purpose a certainty parameter (sometimes also referred to as "uncertainty parameter") corresponding to the level of certainty (or uncertainty) about the profile (cognitive style) and/or an information entropy parameter (the information entropy being a measure of the amount of uncertainty solved by answering the question, as e.g. currently described under the link http://en.wikipedia.org/wiki/Entropy_(information_theory)) corresponding to the expected value of information for determining the cognitive style) in a response of a patient to a certain healthcare provider question.

Figure 4:
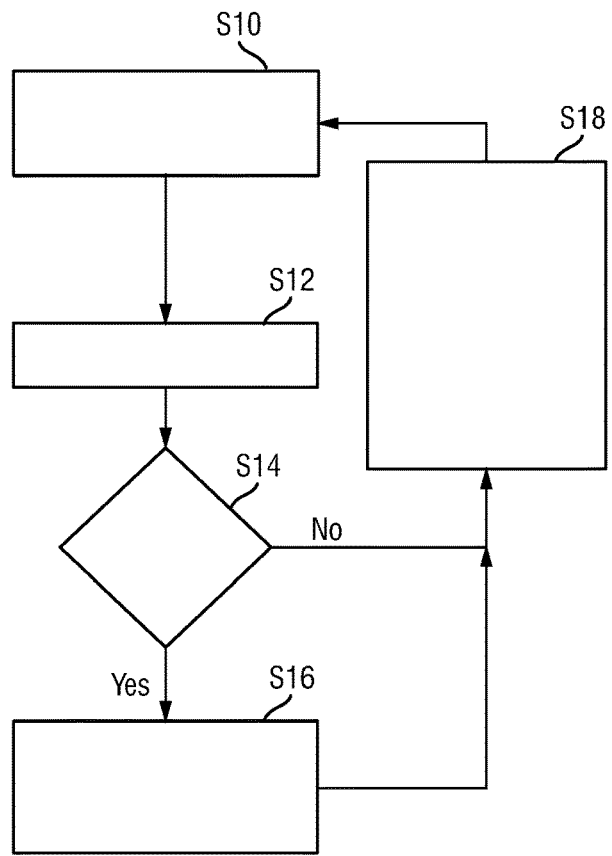
FIG. 4 shows a schematic diagram of an embodiment of a method according to the present invention.
Figure 5:
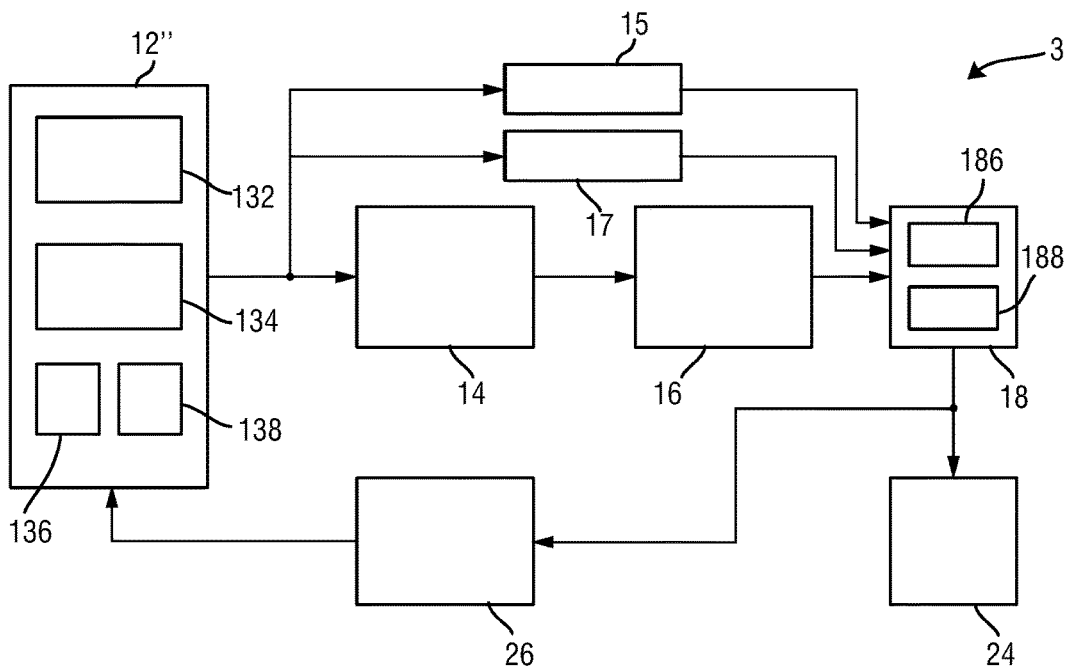
FIG. 5 shows a schematic diagram of a third embodiment of a system according to the present invention.

FIG. 4 shows a schematic diagram of such an embodiment of a method according to the present invention. FIG. 5 shows a schematic diagram of an embodiment of a corresponding system 3 according to the present invention. In a first step S10 the system 3 continuously gathers data from healthcare provider—patient communication unobtrusively. Mainly language extracted from speech collected by another embodiment of an input interface 12" including a microphone 132 or an interrogator (e.g. an interrogator as shown in FIG. 3) is used, but other speech parameters, or features from video and/or physiological signals can also be leveraged. For this purpose, the input interface 12" may further comprise a camera 134 and/or sensors 136, 138 for sensing physiological data, e.g. heart rate sensor or a breathing sensor. The microphone 132, camera 134 and sensors 136, 138 may alternatively be provided as separate elements instead of being included in a common input interface 12" (or a separate apparatus coupled to a simple data input interface).

In step S12 the most dominant cognitive style of the patient is determined by the style identifier 18. The audio data obtained by the microphone 132 are processed by the translator 14 and the language processor 16 as explained above. For processing the video data obtained by the camera 134 and the physiological data obtained by the sensors 136, 138 a video data processor 15 and a physiological data processor 17 are provided.

The video signal can be analyzed to extract certain features. For example, the intensity and frequency of active gestures which can be indicative of a certain cognitive style, in particular when combined with the identification of a certain topic. For example, when more intense gestures are made more frequently by the person when discussing a health topic (identified by recognizing words such as 'health', 'taking medication', 'healthy lifestyle'), this is indicative of an internal Locus of Control instead of an external Locus of Control. Another example would be to extract facial expressions, which can be indicative of a certain cognitive style, in particular when discussing a certain topic, For example, when discussing a new diagnosis (identified by recognizing words such as diagnosis, new prescription, lifestyle change, a facial expression showing despair can be indicative of a particular cognitive style (see Table 1 below), while a facial expression showing self-confidence may be indicative of a different cognitive style.

In a similar manner, physiological signals can be analyzed and are indicative of a certain cognitive style, in particular in combination with the identification of a certain conversation topic. For example, when discussing a new diagnosis and a GSR sensor shows high arousal, this corresponds to discomfort in the person which may be indicative of discomfort and thereby indicative of a different cognitive style then while a low arousal/discomfort level.

The outputs of the language processor 16, the video data processor 15 and the physiological data processor 17 are used by the style identifier 18 to determine the patient's cognitive style, for instance from a lookup table containing the available cognitive styles and the likelihood of being most dominant of each of the cognitive styles for the current patient.

An example of such a table is shown below as Table 1, e.g. stored in a style database 186. Table 1 illustrates an example data scenario for implementing step S12. The invention is not limited to the four cognitive styles used in this example. Each sample number (nr.) can be viewed as one iteration in the method depicted in FIG. 4 (with a sampling frequency of, e.g., 0.05 Hz).

TABLE 1

| | Available cognitive styles | | | | Certainty level (=highest % − second highest) | Cognitive style advice in display mode Certainty levels (certainty %): <15: no advice |
|---|---|---|---|---|---|---|
| Sample nr. | Fighter (F) | Analyst (A) | Optimist (O) | Sensitive (S) | % in columns 2 to 5) | 15-30: small letter, normal font >30: big letter, bold font |
| 1 | 25% | 25% | 25% | 25% | 0 | -empty- |
| 2 | 25% | 35% | 25% | 15% | 10 | -empty- |
| 3 | 25% | 50% | 15% | 10% | 25 | a |
| 4 | 20% | 65% | 10% | 5% | 45 | A |
| 5 | 20% | 70% | 5% | 5% | 50 | A |

Transition from step S10 to step S12, i.e., how speech features help to determine cognitive style is described in detail above.

In step S14 the certainty level is constantly updated by the style identifier 18 in order to change the display mode of the user interface 24 (e.g. a display of a tablet or smartphone) accordingly. This is also indicated in Table 1, right-most column. In case the certainty level has changed, also the display mode is changed in step S16.

In step S18, the information entropy of a set of possible next (open and/or closed) questions is determined by an optimizer 26, preferably based on the information value that is expected to be present in the answer to the question. The optimizer 26 selects the optimal next (obtrusive) question to ask to increase the profile certainty in order to further distinguish between the most dominant and second-most dominant profile. This is preferably done using a style-distinguishing lookup table. An example of such a table is shown below as Table 2, e.g. stored in a style-distinguishing database 188. Table 2 illustrates fragments of a style distinguishing lookup table (illustrating step S18 the method shown in FIG. 4), used to determine the information entropy (right column) of a set of possible next questions (middle column).

TABLE 2

| ID | Styles distinguished | Question | Answer Key (answer = entropy) |
|---|---|---|---|
| 1 | Fighter - Analyst | Will others rather describe you as "Actionable" or "Analytic"? | Actionable = F + 3, A − 3 Analytic = A + 4, F − 4 |
| 2 | Fighter - Analyst | Will others describe you rather as "the boss" or as "the expert"? | The boss = F + 1, A − 1 The expert = A + 2, F − 2 |
| ... | | | |

TABLE 2-continued

| ID | Styles distinguished | Question | Answer Key (answer = entropy) |
|---|---|---|---|
| 28 | Fighter - Optimist | Is life about achieving things, or about enjoying things? | Achieving = F + 8, O − 1 Enjoying = O + 7, F − 6 |
| ... | | | |
| 136 | Sensitive - Optimist | When it comes to healthcare information, do you typically prefer guidance or choice? | Guidance = S + 4, O − 3 Choice = O + 2, S − 2 |
| ... | | | |

When the uncertainty level is below a particular (predetermined) threshold, the optimizer 26 finalizes suggesting new questions and takes the resulting cognitive style as a final result.

An example scenario, using Table 1 and Table 2 could be as follows. After the fifth sample (Table 1), the likelihood percentages of the four available profiles (F, A, O, S) are 20%, 70%, 5% and 5%, respectively, and the certainty level is 50(%). Since F and A have the highest likelihood, the certainty level is calculated from these two profiles (highest-second highest). To further increase the certainty level, it is most effective to further distinguish between F and A. Therefore, the optimizer 26 looks up (see Table 2) questions to distinguish between F and A. Questions with ID1 and ID2 do so, but ID1 has higher entropy values (i.e., a stronger impact on the certainty level, namely 3% or 4% depending on which answer is given). Therefore, the optimizer 26 selects question ID1 to use for interrogating the patient (or, alternatively, displays the question on the user interface 24 so that the healthcare provider can ask this question to the patient).

There are a plurality of further embodiments and improvements of the method and system illustrated in FIGS. 4 and 5.

In an embodiment, the doctor can turn continuous data gathering temporarily off (e.g., to avoid that the system also gathers data about private communication/staff-staff communication or other conversations that are inappropriate.

In an embodiment, cognitive style-advice-success information can be fed back from the person or the healthcare provider to the system, e.g., based on adherence results resulting from the tailored intervention or based on staff-overruling of the system's advice (possibly, staff with expertise regarding the determining of cognitive styles can provide feedback to the system).

In another embodiment, the system can use a feedback loop in which after every profiling interview, it analyses which questions were most instrumental in getting to this specific profile. Based on that analysis, the system (particularly the style identifier 18) changes the entropy data stored in Table 2.

In another embodiment, the systems used by each healthcare provider individually are connected, e.g. using an internet-based protocol, to improve the efficiency of the feedback loop, in particular by aggregating the post-hoc analysis after every profiling interview.

In another embodiment, in addition to (or instead of) displaying a style advice to the healthcare provider, the system may communicate the style advice automatically to other information systems (e.g., for implementation of the tailored communication style).

In another embodiment, the healthcare provider can determine the healthcare provider-patient conversation context, in which the conversation occurs. For instance, a healthcare provider may want to differ between a typical "intake interview" and a typical "exit interview" with a patient. In the intake interview, the patient may know less about his/her disease and therefore the "Need for Cognition" (e.g., implemented as "use of terminology") thresholds mentioned above may be lower than for the typical exit interview. Alternatively, it can take into account the specific specialism of the healthcare provider (e.g., physiotherapist, GP, or cardiologist), to which patients might react differently, or show different characteristics.

In another embodiment, as long as the current cognitive style advice is (still) empty, a progress bar may be used to indicate how many more questions/minutes of conversation the system expects to need before increasing one level of certainty.

Figure 6:
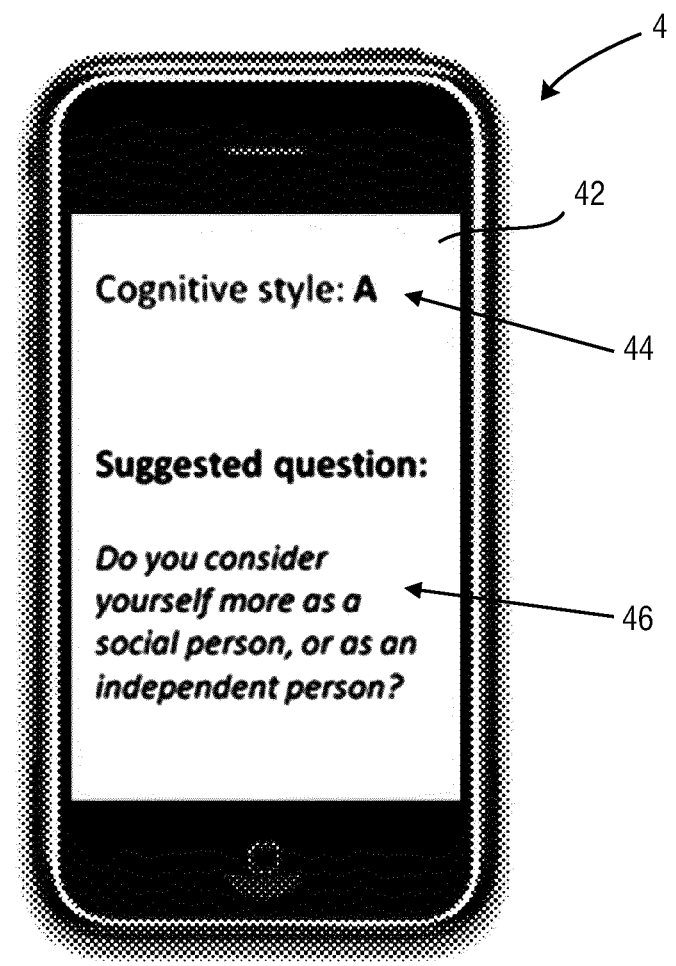
FIG. 6 shows a fourth embodiment of a system according to the present invention in the form of a smartphone.

In another embodiment, in case the certainty level changes, the user can be informed about this change, e.g., by a buzzing smartphone. Such an embodiment is illustrated in FIG. 6. The smartphone 4 represents another embodiment of the system according to the present invention. Available elements of the smartphone, such as the microphone, the loudspeaker, the processor and the storage, are used for implementing the above explained elements and functions of the proposed system. The display 42 of the smartphone 4 is used as user interface that displays the determined cognitive style 44 of the patient and the suggested next question 46.

In another embodiment, the formulation of the style distinguishing questions (see Table 2) can be made more specific/relevant, based on previously gathered data about the healthcare provider's conversation topic. For instance, in case the system has determined that patient's family caregiver is her husband, then the first question in Table 2 can be formulated as "Will your husband rather describe you as Actionable or Analytic?"

The system could also suggest questions that do not ask about the personality style, but content questions for which the system has learned that help in distinguishing between personality styles. For example the question "Do you have any questions regarding the intake of your medication?" will be answered by some patients by asking about the consequences of the medication and by others about details such as if it should be taken with water or milk. The system could even keep track of these sorts of questions, which occur in almost every talk with the physician and check whether these questions are already asked.

In another embodiment, the formulation of the style distinguishing questions (see Table 2) can also be made more appealing/relevant, based on the suggested style advice. For instance, in case the patient uses a lot of terminology (e.g., resulting in a higher certainty level regarding the analyst profile), the style distinguishing questions can be tailored toward that profile (i.e., also containing more terminology).

In another embodiment, the system uses not only language from the patient to obtain the cognitive style, but also specific parameters of the communication from an audio or video signal to determine the cognitive style of the patient. For instance, a fighter might have a more dominant style as expressed by the energy in the speech or the amount of movement of the body, whereas a sensitive might be more submissive, leading to a softer speech.

In another embodiment, the system uses specific parameters of the communication from audio, video or physiology to determine the state of the patient and subsequently use this state to:

Determine the next question, based on the current state of the patient. Certain questions are more effective or ineffective when patients are in a certain state. A feedback loop mechanism as described earlier can be used to learn when asking certain questions are most effective.

Compensate for the state of the patient to better determine the profile, as patients answer differently based on the (emotional) state they are in. By compensating for the state, the answer can be adapted to the answer that would be given when the patient would be in a relatively neutral state.

In another embodiment, an initial non-uniform distribution of probabilities over the profiles is taken into account, based on the natural distribution of the profiles in the specific segment of the patient. This can be specific to certain patient characteristics like demographics or disease, if specific distributions for these characteristics are available. This distribution can change over time based on a feedback loop from the system. That is, every time a new patient is profiled, the a priori distribution of probabilities is changed by adding the profile of the newly profiled patient.

The present invention can further be embodied into a decision support system capable of audio recording, processing and displaying of information. Said decision support system comprises a processor and a computer-readable storage medium, wherein said computer-readable storage medium contains instructions for execution by the processor, wherein said instructions cause said processor to perform the steps of the method according to the present invention.

One possible embodiment is as a smartphone app, which may be used on a smartphone as shown in FIG. 6, carried by a healthcare provider, showing the suggested profile "Analyst". A certain color, font, size and/or other feature of the style indicator indicates the style identifier is not yet fully certain (see also Table 1) and the system-suggested question to achieve more profiling certainty.

Another possible embodiment is a software application on a fixed computer coupled to a microphone and camera that are positioned in the room and can track patient's behavior, physiology, and speech unobtrusively. Subsequently, the audio and video signals are sent to the computer for analysis, and the computer display is used to present the output to the healthcare provider.

Yet another possible embodiment is a pair of glasses that can be worn by the healthcare provider and that contain a microphone and video camera to measure input parameters. These are wirelessly sent to a portable computer like a smartphone that is in the vicinity, e.g. using Bluetooth, which sends back the output which is projected onto the glasses overlaying the healthcare providers field of view. This has the advantage that it is less distracting for the patient because the healthcare provider does not have to move his eyes or head to look at a different display.

The proposed system will assist healthcare providers in adapting their interventions and communication style to the patient. This system will be able to do this by assessing the patient's cognitive style by evaluating a sample of natural speech from the patient. The system will provide recommendations for the most effective intervention to the health care provider based on the patient's cognitive style.

One application of this invention is cognitive style identification of chronically ill patients with medication management challenges. It is of importance to understand their cognitive style in order to determine the optimal information delivery style of the adherence intervention. With this invention a caregiver could be directed to ask the patient a number of open ended questions and record the patient's answer. A system according to the present invention is able to record the answer and translate that into the likely psychographic of that patient.

Figure 7:
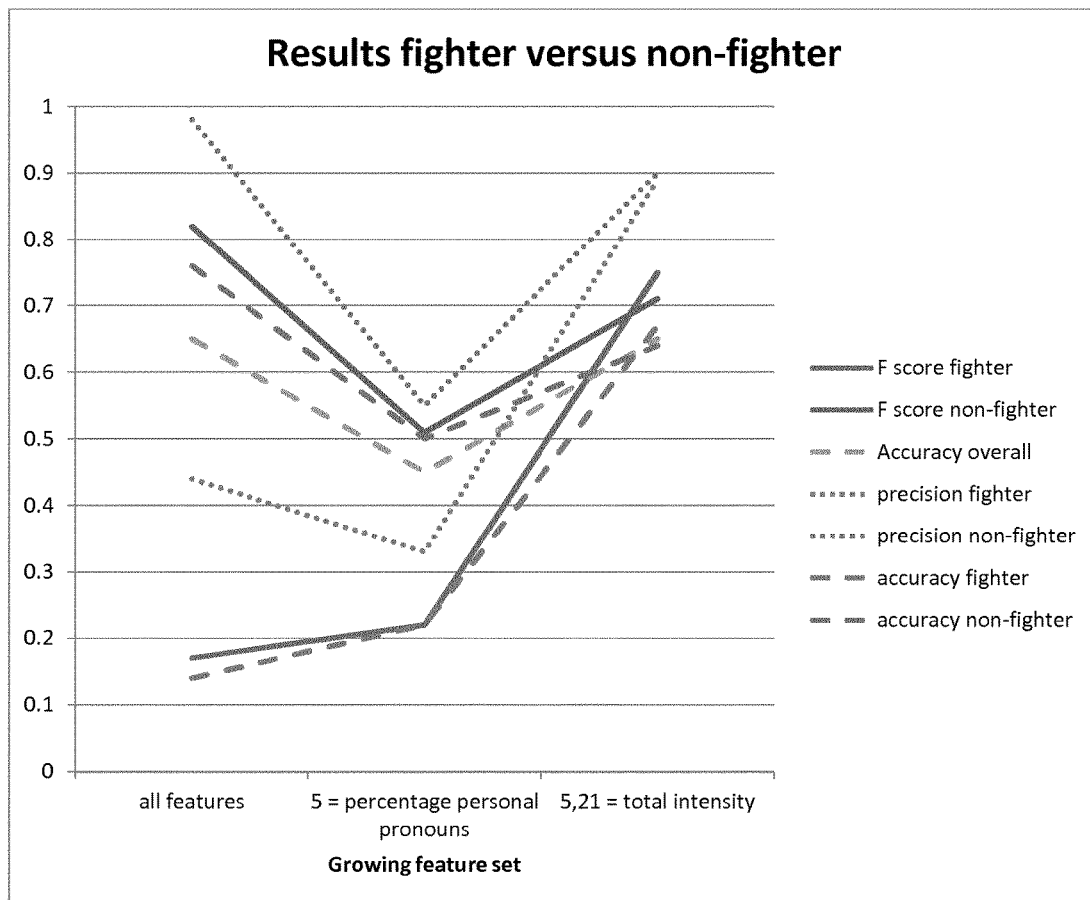
FIG. 7 shows an exemplary plot of the results of a cognitive style versus each another cognitive style.
Figure 7A:
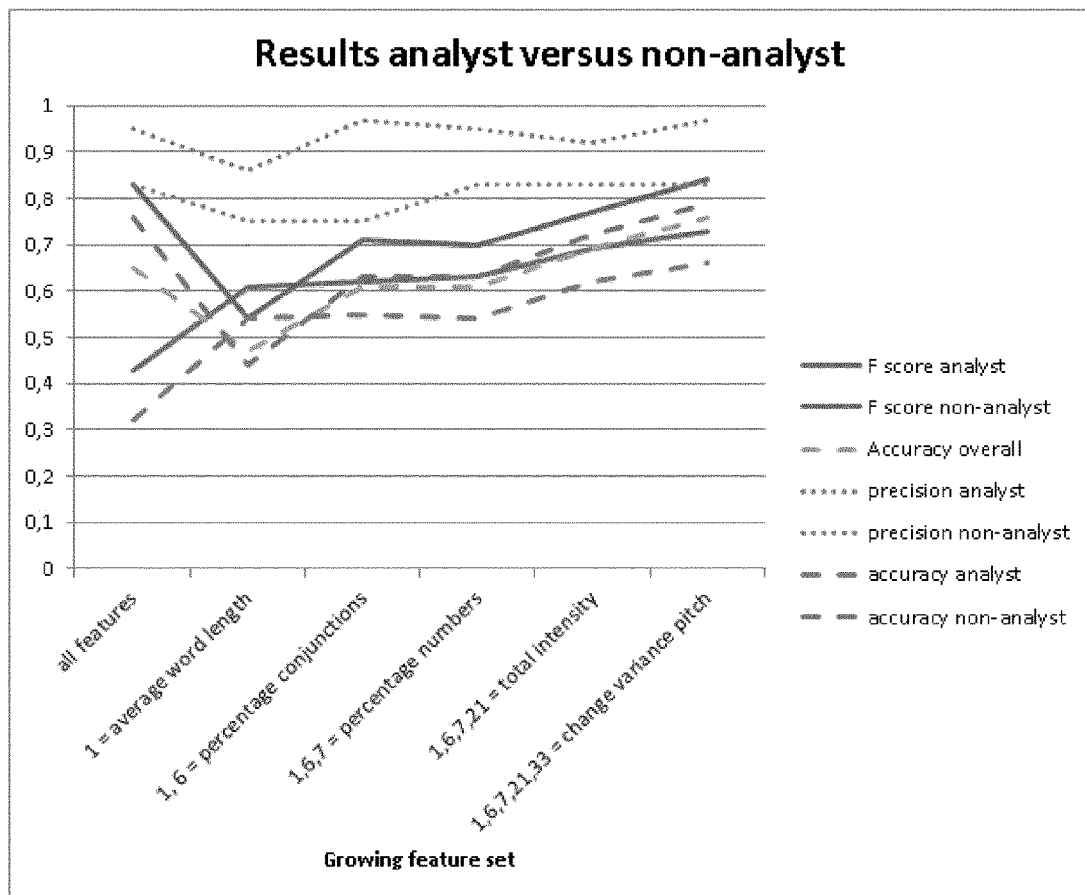
Figure 7B:
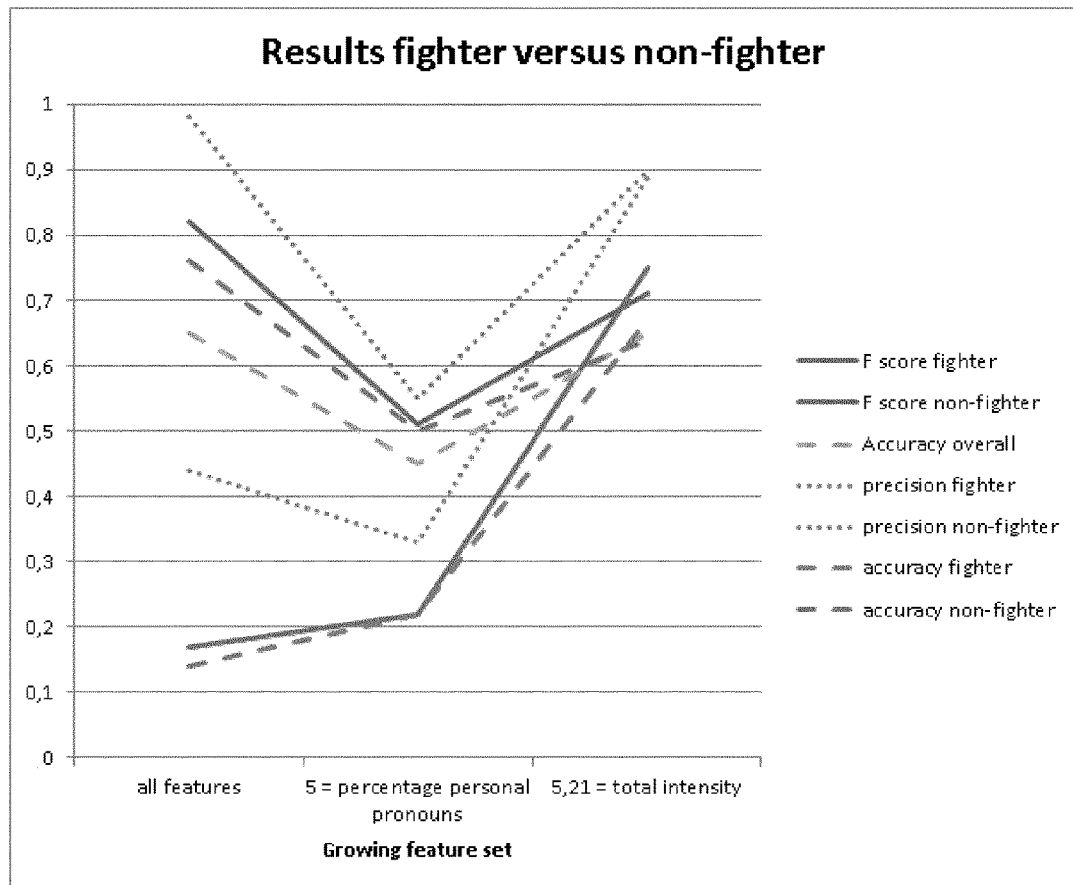
Figure 7C:
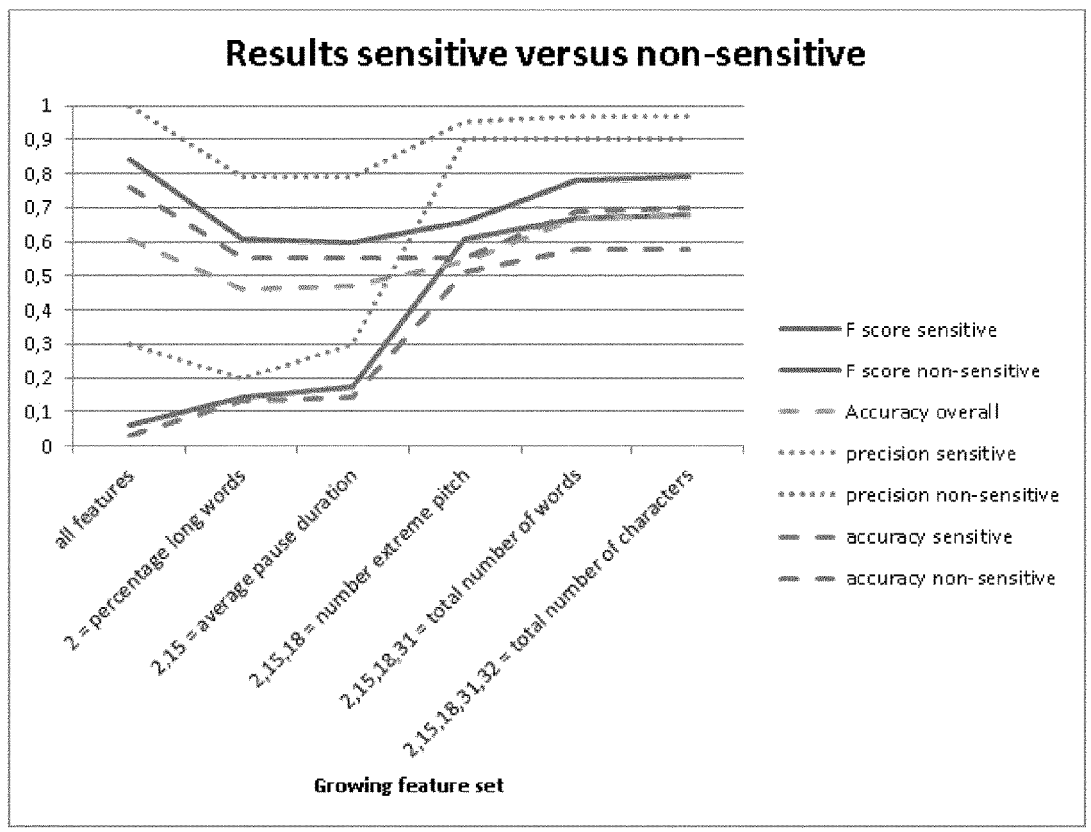
Figure 7D:
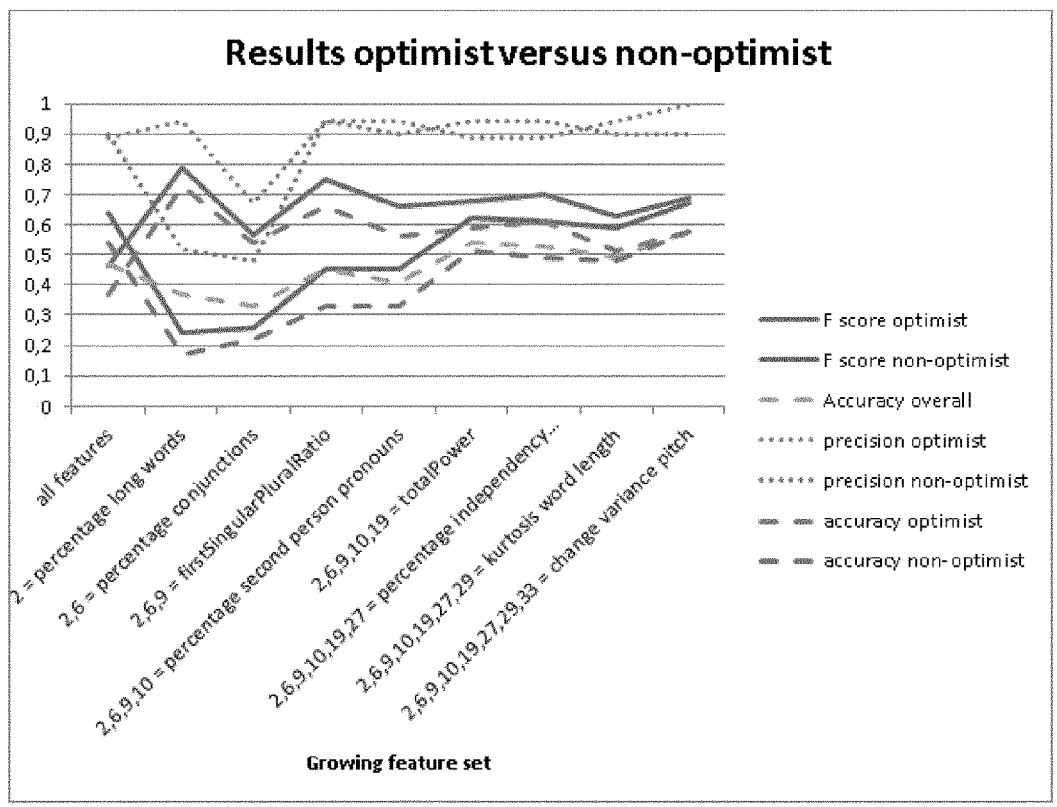

Several classifiers that were interconnected have been developed to demonstrate feasibility of the proposed invention. FIG. 7 graphically shows an example of experimental results of a differentiation of an assessed cognitive style of a person (e.g. Fighter) based on an embodiment of the invention with others cognitive styles (non-Fighter). Predetermined natural language elements have been selected and provided in different classifiers where an assessed cognitive style by the present invention and a known cognitive style assessed by other means have been compared and graphically represented. For this example assessment, word and audio based recognition has been tested.

From FIG. 7, one can appreciate that with the determination of all classified natural language elements, the experiment showed discrimination between the assessed profiles vs. any other profiles. From the combination of all natural language element comprised in a selected classifier, the proposed invention allowed to properly assess the cognitive profile of a user, using text and audio means. The skilled person will understand that the representation is of example only and that a comparison between another chosen cognitive styles with known cognitive styles that are not the assessed one may lead to different results. Moreover, different natural language elements will not be capable of discriminating between more than one cognitive profile with the same efficiency.

Figure 8:
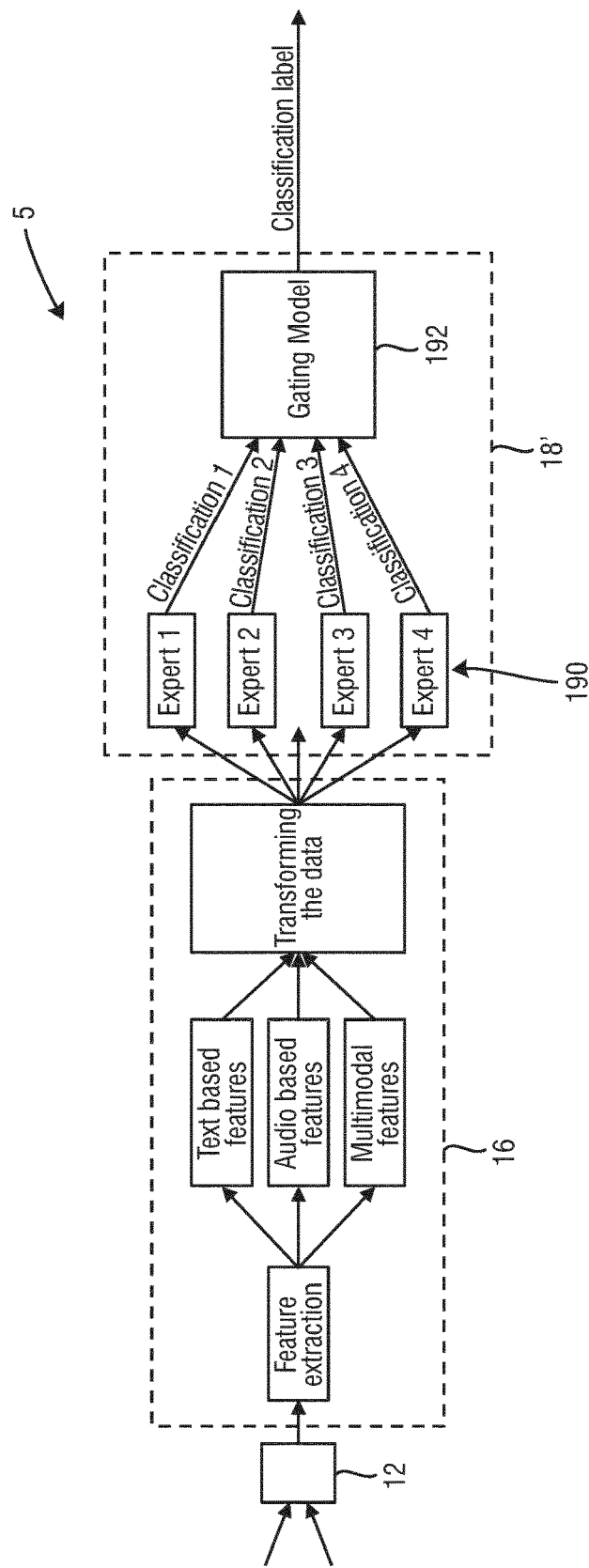
FIG. 8 shows a schematic diagram of a fifth embodiment of a system according to the present invention.

In the following an explanation of another embodiment of the system 5 according to the present invention shall be provided as depicted in FIG. 8. This embodiment focuses on the classification into one of four exemplary cognitive styles: Analyst, Fighter, Optimist, Sensitive. It should be noted, however, that these cognitive styles are to be understood as examples only and that the present invention and this embodiment can be used for the classification of a different number and/or of different cognitive styles as well.

For this classification the proposed style identifier 18' comprises four expert systems 190 that each perform a two-class classification problem (classifying one specific profile against the others), the results of which are fed into a gating model unit 192 that determines the final classification result. The type of expert systems, the language features (herein called natural language elements) used by the expert systems, the gating model and the classification results will be described in detail below.

First, four different machine learning models which are used in different expert systems shall be explained: a multilayer perceptron (MLP), a decision tree constructed with a C4.5 algorithm, a naive Bayes classifier, and a support vector machine (SVM). Descriptions of these models can e.g. be found at Wikipedia or at other sources.

The first machine learning model is a multilayer perceptron (MLP) model, which is a neural network consisting of a layer with input nodes, a hidden layer and an output layer. In an embodiment the input layer consists of nodes in representing a set of selected attributes that belong to a patient. The output layer consists of two nodes representing the possible profiles that can be assigned to a patient. The nodes in between constitute the hidden layer. A mapping from the attributes to the profiles is learned by defining the weights of the edges that minimize the classification error. With every new example the weights are updated with a backpropagation algorithm.

Formally, the classification error that needs to be minimized is defined as $$E(w)=\tfrac{1}{2}\|y(x_n,w)-t_n\|^2$$

where $y(x_n; w)$ is the prediction from the MLP and $t_n$ is the target output. To compute the activations for the hidden and output units of such MLP model the sigmoid function is used:

$$\sigma(v_i) = \frac{1}{1+e^{-v_i}}$$

$$\text{where } v_i = \sum_{i=1}^{N} w_{ij} \cdot \text{input}(i).$$

As the input layer feeds its activation to the hidden layer, the $w_{ij}$ denotes the weights of the edges between the input and hidden units and input(i) is the input provided by the input nodes. For the output layer the $w_{ij}$ are the weights of the edges between the hidden and output notes and input(i) is the activation output of the hidden nodes. How large the changes in weights need to be every iteration is defined using gradient descent:

$$\Delta w_{i,j}(n) = \eta \cdot \frac{\partial E(n)}{\partial v_j(n)} y_i(n)$$

Here $y_i(n)$ is the output for unit n and $\eta$ is a learning rate. All features are nominal. In an embodiment these features are transformed to binary features as well as normalized. The number of nodes in the hidden layer is set at #attributes+ #classes/2 and therefore depends on the feature set and whether the two-class or four-class problem shall be considered. The stopping criterion for training is set at 500 iterations.

A second machine learning model is a C4.5 machine learning model which shall be explained using an example. A decision tree is constructed with the C4.5 algorithm by analyzing which of the selected attributes belonging to a patient is the best one to split on, i.e. to distinguish between profiles. This best attribute is the attribute that yields the highest information gain when this attribute is used for splitting. Information gain is defined as follows:

$$IG(T,a)=H(T)-H(T|a)$$

where H denotes information entropy. In words, the information gain describes the difference in the information entropy of the state before splitting and the information entropy of the state after splitting has occurred with that attribute. Information entropy is defined as:

$$H(T) = -\sum_{i} P(t_i)\log_b P(t_i)$$

where $P(t_i)$ is the probability that $T=t_i$, i.e. that T has class value $t_i$. Splitting along a path in the tree continues until a base case is encountered. There are three base cases:

1. No attribute provides any information gain.
2. All instances in a group resulting from splitting belong to the same class. In this case a decision node higher up in the tree is created using the expected value of the class.
3. A new class is encountered. Again a decision node higher up in the tree is created. The resulting decision tree is the trained machine learning model. This tree can be pruned in order to remove any decision nodes that do not contribute to classification.

For the third model, a naive Bayes classifier model, the simplest probabilistic machine learning model shall be used: a naive Bayes (NB) classifier. It is considered simple because it assumes that every attribute that describes a subject is independent from all the other attributes. As this independence assumption not always holds for the dataset, it is referred to as a naive approach As a result of its simplicity, learning a model is very fast and is useful for problems for which time is an issue.

The naive Bayes classifier is based on Bayes' theorem:

$$P(C=c_i|A_1,\ldots,A_n) = \frac{P(C=c_i)\cdot P(A_1,\ldots,A_n|C=c_1)}{P(A_1,\ldots,A_n)}$$

$P(C=c_i)$ is the probability that for a particular subject the class value is $c_i$ while $P(A_1,\ldots,A_n)$ is the probability that the attributes $A_1,\ldots,A_n$ have a specific value. Using the independence assumption we can now compute $P(C=c_i|A_1,\ldots,A_n)$ using the naive Bayes approach as follows $$P(C=c_i|A_1,\ldots,A_n) = \frac{P(C=c_i)\cdot P(A_1|C_1=c_i)\cdot\ldots\cdot P(A_n|C=c_i)}{P(A_1,\ldots,A_n)}$$

$$= \frac{P(C=c_i)\cdot \prod_{j=1}^{n} P(A_j|C=c_i)}{P(A_1,\ldots,A_n)}$$

Normally the factor $$\frac{1}{P(A_1,\ldots,A_n)}$$

is called a scaling vector and is replaced by 1/Z, such that Bayesian computation can be written as follows:

$$P(C=c_i|A_1,\ldots,A_n) = \frac{1}{Z}\cdot P(C=c_i)\cdot \prod_{j=1}^{n} P(A_j|C=c_i)$$

The $c_i$ for which $P(C=c_i|A_1,\ldots,A_n)$ is the highest that is assigned as the label to the instance.

The three models considered so far are fairly simple and are easy to build. However, sometimes a problem requires a mathematically more complex classification model. As an example of such more complex classification, for the fourth machine learning model, a support vector machine (SVM) is considered. The workings of an SVM are based on the observation that some classification problems cannot be solved because the data cannot be separated in two or more classes in the current feature space. However, a solution may be obtained by considering the problem in another feature space to achieve that the aim is to compute a kernel, a mathematical transformation that transforms the data to another feature space such that data does become separable. For instance, a separation between instances of Analyst and non-Analyst profile can be made, as will be explained in more detail below. Around the decision boundary there is a margin, which is defined as m/||w||, where m is the distance between the decision boundary and the nearest training instances expressed in vector w.

Within the construction of a support vector machine, the goal is to find the decision boundary that minimizes this margin. As m is normally set to one this is equivalent to minimizing w. Specifically, the goal is to minimize $0.5\|w\|^2$. Minimization is achieved using Lagrange multipliers. The important thing to keep in mind is that the best decision boundary has the smallest margin.

The data can be transformed using a polynomial kernel. This kernel is used to represent the original data in another feature space, specifically a feature space over polynomials of the original training data instances. If there are two vectors of the input space $x_i$ and $x_j$, the polynomial kernel is defined as follows:

$$K(x_i,x_j)=(1+x_i \cdot x_j)^d$$

where d is the degree of the polynomial. Further, the support vector machine can be optimized using the SMO algorithm.

Now that four different machine learning techniques have been defined, those can be applied to find the best models for every expert problem. Each of these models will receive a subset of the audio, text and multi-modal features as input. Next to providing a classification for each instance, it produces for each instance class-confidences. These class-confidences are measures of how certain the model is that this specific instance is of that class-type. Each model therefore produces two confidence values, one for the C profile (class profile) and one for the non-C profile. In this context C is used here to refer to one of the four cognitive styles: Fighter, Analyst, Optimist, or Sensitive. So basically the expert systems are trained to distinguish Analyst from non-Analyst profiles, Fighter from non-Fighter profiles etc. The confidences for each C-profile will be used, the one that an expert should specialize in, as input to the gating models. The gating methods receive a set of four different confidences, each one representing the certainty that an instance is of type C.

With this embodiment a differentiation task between four different profiles shall be achieved. In machine learning terms, the task is to learn how to classify specific with the correct profile label. As explained above several machine learning models are considered to find the model that classifies the patients in the most optimal way. Specifically, the model for which the unweighted average recall is optimal is adopted. The unweighted instead of the weighted average recall has been chosen because classification performance for each profile is equally important.

A possible solution consisting of a mixture of four weak classifiers has been defined, each serving as an expert to differentiate between one profile and the rest. For these four sub-problems, the model that yields the most optimal profile assignment in terms of the unweighted average recall shall be found. In the following the one-profile-against-all classification tasks will be described per profile.

A brief summary of the profile definition will be given to explain what kind of patients that profile describes. Further, performance results and feature sets that yield highest performance will be described. Significance shall be understood as statistical significance as proven with a statistical test.

An Analyst profile applies to patients who take their disease very seriously. They try to obtain as much knowledge about their disease in order to feel in control. They are organized in dealing with their disease. As they know a lot about their disease, they tend to be specific about the details, e.g., years, dosages, and names of medication.

According to the performance results for differentiating between the Analyst profile and the rest, the MLP is the best performing model since it yields the highest average recall. This notion is further supported by the mean standard error (MSE) which is the lowest for MLP as well. This lowest MSE means that the model is more certain about its label assignments than any of the other models. Recall that MSE can be decomposed into bias and variance. Therefore, the MLP yields the best trade-off between overfitting (large variance) and underfitting (large bias) the data. If compared to the two baselines ZeroR and random it is found that the MLP model is significantly better than ZeroR for predicting the Analyst profile and significantly better than random for predicting both the Analyst and non-Analyst profile. In short, the MLP is defined as the best classifier for this problem. Overall, the mean standard error is relatively low for all models applied to the Analyst versus non-Analyst dataset (except for the C4.5 decision tree). This overall low MSE indicates that a machine learning approach is most successful for this particular problem as the models are the most confident in assigning the labels. Low MSE indicates that a machine learning approach is most successful for this particular problem as the models are the most confident in assigning the labels.

For each classification model the optimal feature set for differentiating patients with Analyst profile from other patients has been defined. The optimal feature set for the optimal MLP model consists of five different features: average word length, percentage numbers, percentage conjunctions, total intensity in decibel (dB) and the variance in change of the pitch value over time. With increasing recall the mean squared error overall decreases, with maximum recall and minimum mean squared error for the final feature set. The recall is lower and MSE is higher if all the features are used which shows the importance of performing feature selection.

Patients with Analyst profile may use longer words on average and may be very detailed about dosages, numbers, medication and other names. Such words tend to be longer than more frequent words, especially in English.

Secondly, patients with Analyst profile may use fewer conjunctions than other patients. Specifically, conjunctions like "and" and "or" may also be used to fill up any pauses in the sentences.

The last text feature in the feature set is the percentage of numbers. The previous fragment shows that numbers are used a lot, but the means do not differ between Analyst and non-Analyst patients.

The biggest difference in means is observed for the sound feature total intensity. Analyst patients talk louder. However, talking loudly is not necessarily a characteristic one would expect to belong to a patient with Analyst profile. However, the observation that Analyst patients have high total intensity may be due to a good position of the microphone and is not necessarily a specific determinant for the Analyst profile.

Finally, the last feature of the optimal feature set is the change variance in the pitch value. As this value is lower for Analyst patients this indicates that they talk with a more monotonous voice than other patients.

For all these feature means, standard deviation is high. This indicates that there is a lot of variance within each profile class which highlights the difficulty of the current problem. However, the standard errors are acceptable (with exception of the percentage numbers), i.e. the means of the dataset are fairly close to the population mean. This explains why classification is still possible, despite the high variance in the dataset and within each profile class.

Patients with Fighter profile may deal with their disease in a very active way. They may be in charge and in control. They may just want to know what to do in order to fight their disease, but cannot be bothered with too many details. These patients may be considered to be to the point.

Performance results for differentiation between the Fighter and non-Fighter patients show that the MLP model yields the highest average unweighted recall which is explained by relatively high performance for both predicting Fighter and non-Fighter profile. In this case the MSE is not minimal for the MLP, but is somewhat higher than the lowest value which is the C4.5 decision tree. As the average recall is substantially lower for the model that does yield the lowest MSE, the MLP is adopted as the best performing classifier. The MLP is proven to perform significantly better than the two baselines for both prediction of Fighter and non-Fighter patients. Based on these results, the MLP is defined as the best classifier for this problem.

For each model applied to the Fighter profile dataset, the optimal feature set has been defined. The highest performance overall for classifying this dataset is achieved with the MLP for which the optimal feature set consists of the percentage personal pronouns and the total intensity in dB. The average performance is higher for the optimal feature set than the performance for the complete feature set. However, the mean squared error is the same which means that the bias-variance tradeoff is not improved with feature selection. On the other hand, it does show that higher performance can be achieved with only a limited set of features without impairing the bias-variance trade-off. The size of the feature set is also an advantage in terms of the model complexity; two features means only two inputs in the MLP, which leads to fewer hidden nodes. This reduces the overall complexity of the MLP model and the mapping of inputs to outputs the model needs to learn.

Patients with Fighter profile may use more personal pronouns, such as I, me, she, them. However, over the whole dataset the difference in means is only minimal, especially as the standard deviations show high variance within the profiles.

A substantially large difference is observed for the feature total intensity. Patients with Fighter profile are very direct and dominant which may coincide with a loud voice. The opposite is the case in the current dataset: Fighter patients talk in a softer voice on average, although the high variance suggests that this is certainly not the case for every Fighter patient. Like in the Analyst dataset, this feature probably suffers from a bias caused by inconsistent recording conditions.

The Sensitivity profile is assigned to patients who have a very hard time dealing with their disease. They feel that they are a victim of the disease and that it has taken over their life. They therefore tend to dwell on the past. Patients with Sensitivity profile can seem quiet and depressed and are often more dependent on others.

The performance results for differentiating between Sensitivity patients and non-Sensitivity patients show that the C4.5 decision tree model yields the highest unweighted average recall. This performance is particularly caused by the high recall for predicting patients with the Sensitivity profile. However, the mean squared error for this model is second highest of all the models. This model performs significantly better than the ZeroR classifier with respect to the non-Sensitivity patients, and significantly better than the random classifier with respect to the Sensitivity profile. As the high error values suggest, for this particular problem it is the most difficult to define the best classifier.

The optimal feature set for the C4.5 decision tree as the most suitable profile for the current problem consists of percentage function words, percentage personal pronouns, percentage third person pronouns, text length in words per minute and average time answering. Like in the case of differentiating between Fighter and non-Fighter patients, the optimal feature set yields the highest performance and only a slightly larger mean squared error than the complete feature set. The differences in the features are small, with high standard deviations. Some of the larger differences can be found in the data. The largest differences in means can be found for the text length (words) and the average time it takes per answer. Both values are lower than the averages for the Sensitivity profile highlighting the difference with other profiles.

Patients with the Optimist profile may try to focus on the nice things in life instead of on their disease. They may go with the flow and may be focused on the present. These patients may have no problem undergoing treatment as long as it does not interfere with their lives.

A C4.5 decision tree yields the highest unweighted average recall for differentiation between patients with Optimist profile and others. For all four models, this model results in the highest recall for both prediction of Optimist and non-Optimist patients. The mean squared error for the C4.5 decision tree is substantially lower than all the other errors. The C4.5 decision tree yields the best bias-variance trade-off and is the most suitable classifier for this problem. Furthermore, the C4.5 decision tree performs significantly better for both Optimist and non-Optimist patient prediction when compared to the random classifier. However, the model is only significantly better for non-Optimist patient prediction when compared to the ZeroR classification. This is to be expected since ZeroR performance for Optimist patients is 100% as it is always the most frequent profile. Therefore each of our more sophisticated classifiers will do worse than this ZeroR classifier for predicting Optimist and non-Optimist patients.

For this particular problem all models yield a relatively high mean squared error. This indicates that all the models here are sensitive to outliers and are not complex enough to really fit to the training data. More data will be needed to ensure that the machine learning learns enough examples to predict previously unseen patients.

The C4.5 decision tree results in the highest performance and the lowest error so that the C4.5 decision tree is defined as the model that is most suitable for the current task. The optimal feature set in this case consists of five different features: percentage function words, percentage numbers, the ratio between past and present verbs, the average subjectivity per sentence and finally the variance in how the power changes over time. The Optimist profile is the only profile class for which content-related features play a role in differentiation, for the classifiers that have been defined as most suitable for the different tasks. The mean squared error and the average performance show the same kind of relation as for Analyst profile classification: with increasing performance the error decreases. The performance is maximal and error is minimal for our optimal feature set. Using all the features results in lower performance and higher error, which emphasizes the advantage of feature selection.

Total intensity has been found to be an important feature for differentiating between Analyst patients and the rest and Fighter patients and the rest. For the Sensitivity profile text length (in words) contributes significantly indicating that the less a patient talks, the more likely it is a Sensitivity patient. The Sensitivity profile is the only profile that does not rely on pure audio features showing what only text and multi-modal features can do. Finally, text, audio and multi-modal features are all represented in at least one of the feature sets for the profiles. This highlights the need for using information from multiple modalities, instead of using only audio or text.

In the following, results are described for the use of different gating models. Two general ways of gating the expert outputs are considered:

1. It is assumed that classification of each sample belonging to one participant is independent from the classification output of other samples in the same set. This approach is called independent classification. Four different gating classifiers are considered in this category: MLP, C4.5 decision tree, naive Bayes classifier and support vector machine.
2. It is assumed that classification of each sample belonging to one participant is dependent on the classification output of the other samples within the same set. This approach is called joint classification. The joint classification gating model is the conditional random field (CRF).

The resulting model is best at differentiating between Analyst and Fighter patients and worst at differentiating Analyst and Optimist patients, as well as between Fighter and Optimist patients. In short, the best model for the current task is the mixed mixture-of-experts with an SVM as gating mechanism. This model is found to be significantly better for prediction of the Analyst, Sensitivity and Optimist profile when compared to a random classifier. When compared to the ZeroR baseline prediction of the model is significantly better for prediction of Analyst, Fighter and Sensitivity profile. The current results hold for the assumption that every separate data point of a patient should be considered independent from any other data point.

The final set of results describes what can be observed if the joint classification approach, a conditional random field, is used as gating classifier. Leave-one-patient-out validation is used for each combination of mixture-of-experts with a CRF classifier to define which combination of mixture-of-experts with a CRF best suits the current problem. Based on the results described above the mixed mixture-of-experts should yield the highest results.

It can be concluded that a mixture-of-experts consisting of two MLPs and two C4.5 decision trees gated with a support vector machine is the most suitable model for differentiation between the four different profiles. This particular model was proven to perform significantly better than the two baselines for three profiles.

The independence assumption works best. However, this does not mean that it can be concluded that every data point is independent from any other data point. Rather, the poor performance of the CRF is due to the high variance within each patient such that the dependence assumption is too strict a constraint on this data. In other words, the difference between data points of one patient is already large such that demanding that they all have a similar label is inconvenient. This constraint weights more heavily in the CRF due to the dependence assumption. In short, under the current conditions the mixed mixture-of-experts using an SVM gating method is considered as the overall best model for the problem.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system comprising:
one or more physical processors programmed with computer instructions that, when executed, cause the one or more physical processors to:
receive speech spoken by a person;
analyze the speech to identify natural language elements related to the speech;
determine first and second candidates of cognitive styles for the person based on the natural language elements;
determine a stimulus based on the first and second candidates of cognitive styles and presenting the stimulus to the person;
receive a response to the stimulus from the person;
select, based on the response to the stimulus, one of the first or second candidates as a cognitive style of the person, where the cognitive style indicates a way the person thinks, perceives, and processes information, wherein the cognitive style is different than a mood or an emotional state of the person; and
generate recommendations for tailoring the communication and/or information delivery style to be provided to the person according to the selected cognitive style of the person.

2. The system of claim 1, wherein determining the first and second candidates of cognitive styles comprises:
determining likelihoods of cognitive styles being a dominant cognitive style based on the natural language elements; and
determining the first and second candidates of cognitive styles as dominant cognitive styles based on the first and second candidates of cognitive styles having a highest likelihood and second highest likelihood of the determined likelihoods, respectively.

3. The system of claim 1, wherein the one or more physical processors are caused to:
calculate an uncertainty parameter of the first and second candidates being the cognitive style of the person based on the response to the stimulus; and select one of the first or second candidates as the cognitive style of the person based on the uncertainty level of first or second candidates being below a predetermined threshold.

4. The system as claimed in claim 1, further comprising a translator for translating the received speech into text, wherein the one or more physical processors is configured to analyze the text to identify the natural language elements.

5. The system as claimed in claim 1, wherein the one or more physical processors is configured for generating recommendations on how to tailor healthcare and guidance information to be provided to the person according to the selected cognitive style of the person.

6. The system as claimed in claim 1, further comprising an output interface configured for outputting the selected cognitive style and the generated recommendations for use by a caregiver for tailoring healthcare and guidance information to be provided to the person, and wherein the selected cognitive style includes one or more of extrovert, introvert, fighter, analyst, optimist, or sensitive.

7. The system as claimed in claim 1, further comprising a translator for translating the received speech into text, and wherein the one or more physical processors is configured to determine in the received speech and/or the text one or more of:
an amount and/or length of pauses,
a length of sentences and/or words,
an amount of words in a sentence,
an amount of verbs, nouns, adjectives, personal pronouns and/or possessive pronouns,
an amount of words with predetermined prefixes and/or endings,
an amount of layman's words or phrases,
an amount how much the person speaks about a predetermined topic,
a percentage of second person words, and/or
a variance in pitch.

8. The system as claimed in claim 4, wherein
the translator is configured to determine the language of the received speech; and
wherein the one or more physical processors is configured to analyze the text to identify predetermined natural language elements of the determined language.

9. The system as claimed in claim 1, wherein the one or more physical processors comprises a rule based engine for determining dimensions of the first and second candidates of cognitive styles based on the identified natural language elements.

10. The system as claimed in claim 1, further comprising an input interface, the input interface comprising an audio data interface for receiving audio data files of recorded speech and/or an audio recording unit, in particular a microphone, for converting spoken speech into electric speech signals and/or an interrogator for interrogating the person.

11. The system as claimed in claim 1, further comprising an input interface, the input interface comprising a video data interface for receiving image data files containing image data of the person and/or an imaging unit, in particular a camera, for recording image data of the person,
wherein the system further comprises a video data processor for analyzing the image data to identify predetermined image elements, and
wherein the one or more processors is configured to determine the first and second candidates of cognitive styles based on the identified natural language elements and the identified image elements.

12. The system as claimed in claim 1, further comprising an input interface, the input interface comprising a physiological data interface for receiving physiological data files containing physiological data of the person and/or a physiological data unit, in particular physiological data sensors, for recording physiological data of the person,
wherein the system further comprises a physiological data processor for analyzing the physiological data to identify predetermined physiological data elements, and
wherein the one or more processors is configured to determine the first and second candidates of cognitive styles based on the identified natural language elements and the identified physiological data elements.

13. The system as claimed in claim 1, wherein the one or more processors is configured to determine a dominant momentary cognitive style of the person and a momentary certainty level indicating a likelihood of the selected cognitive style being the dominant style.

14. The system as claimed in claim 13, further comprising:
an interrogator for interrogating the person; and
an optimizer for determining information entropy of one or more possible next questions which may be used for interrogating the person and for selecting a possible next question providing a high information entropy.

15. The system as claimed in claim 1, wherein the one or more processors comprises one or more expert systems, each for performing a two-class classification for classifying if the person falls into one particular cognitive style or not.

16. The system as claimed in claim 15, wherein the one or more processors comprises two or more expert systems and a gating model unit for determining a final classification from the two-class classifications performed by the two or more expert systems.

17. A method for assessing a cognitive style of a person, the method comprising the steps of:
receiving speech spoken by a person;
analyzing the speech to identify natural language elements related to the speech;
determining first and second candidates of cognitive styles for the person based on the natural language elements;
determining a stimulus based on the first and second candidates of cognitive styles and presenting the stimulus to the person;
receiving a response to the stimulus from the person;
selecting, based on the response to the stimulus, one of the first or second candidates as a cognitive style of the person, where the cognitive style indicates a way the person thinks, perceives, and processes information, wherein the cognitive style is different than a mood or an emotional state of the person; and
generating recommendations for tailoring the communication and/or information delivery style to be provided to the person according to the selected cognitive style of the person.

* * * * *